US00PP26838P2

(12) United States Plant Patent
Zaiger et al.

(10) Patent No.: US PP26,838 P2
(45) Date of Patent: Jun. 21, 2016

(54) PEACH TREE NAMED 'SNOW SPRITE'

(50) Latin Name: *Prunus persica*
Varietal Denomination: Snow Sprite

(71) Applicants: Gary Neil Zaiger, Modesto, CA (US); Leith Marie Gardner, Modesto, CA (US); Grant Gene Zaiger, Modesto, CA (US)

(72) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 51 days.

(21) Appl. No.: 14/544,253

(22) Filed: Dec. 15, 2014

(51) Int. Cl.
*A01H 5/08* (2006.01)

(52) U.S. Cl.
USPC ..... Plt./195

(58) Field of Classification Search
USPC ..... Plt./195
See application file for complete search history.

*Primary Examiner* — Anne Grunberg

(57) ABSTRACT

A new and distinct variety of peach tree (*Prunus persica*). The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. A regular and productive bearer of large size, clingstone fruit.
2. Fruit with an attractive skin color.
3. Fruit holding firm on the tree 7 to 8 days after maturity (shipping ripe).
4. Fruit with a mild, sweet, subacid flavor.
5. Vigorous, upright growth of tree.

1 Drawing Sheet

Botanical designation: *Prunus persica.*
Variety denomination: 'Snow Sprite'.

BACKGROUND OF THE VARIETY:

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of peach tree was originated and asexually reproduced by us in our experimental orchard located near Modesto, Stanislaus County, Calif.

PRIOR VARIETIES

Among the existing varieties of peach and nectarine trees, which are known to us, and mentioned herein, 'Red Grand' Nectarine (U.S. Plant Pat. No. 1,060), 'Red Wing' Peach (U.S. Plant Pat. No. 621), 'Sugar Lady' Peach (U.S. Plant Pat. No. 7,532), 'O'Henry' Peach (U.S. Plant Pat. No. 2,964), 'May Grand' Nectarine (U.S. Plant Pat. No. 2,794), 'Rich Lady' Peach (U.S. Plant Pat. No. 7,290), 'Sweet Dream' Peach (U.S. Plant Pat. No. 10,176) and our proprietary non-patented peach seedling selections '233LK471' and '373LH55'.

STATEMENT REGARDING FEDERALLY SPONSORED RESEARCH AND DEVELOPMENT

Not applicable.

ORIGIN OF THE VARIETY

The new and distinct variety of peach tree (*Prunus persica*) was developed by us in our experimental orchard located near Modesto, Calif. as a first generation cross between two proprietary non-patented peach seedlings with the field identification numbers '233LK471' and '373LH55'. The seed parent (233LK471) originated from crosses between the following varieties; 'Red Grand' Nectarine (U.S. Plant Pat. No. 1,060), 'Red Wing' Peach (U.S. Plant Pat. No. 621), 'Sugar Lady' Peach (U.S. Plant Pat. No. 7,532), 'O'Henry' Peach (U.S. Plant Pat. No. 2,964) and 'May Grand' Nectarine (U.S. Plant Pat. No. 2,794). The pollen parent (373LH55) originated from crosses between the following varieties; 'O'Henry' Peach (U.S. Plant Pat. No. 2,964), 'Sugar Lady' Peach (U.S. Plant Pat. No. 7,532), 'Rich Lady' Peach (U.S. Plant Pat. No. 7,290) and 'Sweet Dream' Peach (U.S. Plant Pat. No. 10,176). A large group of these first generation seedlings were planted and maintained on their own root system, during which time we recognized the desirable trees and fruit characteristics and selected it in 2003 for additional asexual propagation and commercialization.

ASEXUAL REPRODUCTION OF THE VARIETY

In 2003 asexual reproduction of the new and distinct variety of peach tree was by budding to 'Nemagaurd' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The new variety of peach tree (*Prunus persica*) is of large size, vigorous, upright growth and is a productive and regular bearer of large, white flesh, clingstone fruit that has a mild, sweet, subacid flavor and excellent eating quality. The fruit is further characterized by having firm flesh with the ability to remain firm on the tree 7-8 days past maturity (shipping ripe), attractive red skin color and being relatively uniform in size and maturity throughout the tree. In comparison to its seed parent (233LK471), the new variety is more productive and matures approximately 20 days later. In comparison to its pollen parent (373LH55) the fruit of the new variety has white instead of yellow flesh and matures approximately 20 days later. In comparison to the commercial variety 'Snowfall' Peach (U.S. Plant Pat. No. 11,568) the fruit of the new variety matures approximately 6 days earlier.

DESCRIPTION OF THE PHOTOGRAPH

The accompanying color photographic illustration shows typical specimens of the foliage and fruit of the present new peach variety.

The illustration shows the upper and lower surface of the leaves, an exterior and sectional view of a single fruit divided in its suture plane to show flesh color, pit cavity and the stone remaining in place.

The photographic illustration was taken shortly after being picked (shipping ripe) from a 10 year old tree and the colors are as nearly true as is reasonably possible in a color representation of this type.

DESCRIPTION OF THE VARIETY

The following is a detailed botanical description of the new variety of peach tree, its flowers, foliage and fruit, as based on observations of 10 year old specimens grown near Modesto, Calif., with color in accordance with Munsell Book of Color published in 1958.

Tree:

*Size*.—Large, usually pruned to 3 to 3.5 meters in height and width for economical harvesting of fruit. Size varies with different cultural practices.

*Vigor*.—Vigorous, growth of 1.5 to 2 meters the first growing season. Varies slightly with soil type, fertility of soil and climatic conditions.

*Form*.—Upright, usually pruned to vase shape.

*Branching habit*.—Upright, crotch angle approximately 35°, increases with heavy crop load.

*Productivity*.—Productive, thinning and spacing of fruit necessary for desired market size. Fruit set varies with climatic conditions during bloom time.

*Bearer*.—Regular, adequate fruit set 8 consecutive years. No alternate bearing observed.

*Fertility*.—Self fertile.

*Density*.—Medium dense, pruning to vase shape desirable for sunlight penetration to center of tree to enhance fruit color and health of fruit wood.

*Hardiness*.—Hardy in all stone fruit growing areas of California. Tree grown in USDA Hardiness Zone 9. Winter chilling requirement approximately 900 hours at or below 45° F.

Trunk:

*Size*.—Large. Average circumference 54.6 cm at 22.9 cm above ground on a 10 year old tree.

*Stocky*.—Medium stocky.

*Texture*.—Medium shaggy, roughness increases with age.

*Color*.—Varies from 7.5YR 2/4 to 10YR 4/2.

Branches:

*Size*.—Medium. Average circumference 13.5 cm at 1.2 meters above ground. Crotch angle approximately 35°, increases with heavy crop load.

*Surface texture*.—New growth relatively smooth. Mature growth medium rough, roughness increases with age.

*Lenticels*.—Average number 32 in a 25.8 square cm section. Average length 5.0 mm. Average width 1.9 mm. Color varies from 7.5YR 5/8 to 10YR 5/8.

*Color*.—New growth varies from 5GY 5/6 to 2.5GY 8/4. Mature growth varies from 7.5YR 3/4 to 7.5YR 2/4, varies with age of growth.

Leaves:

*Size*.—Large. Average length 145.9 mm. Average width 43.8 mm.

*Form*.—Lanceolate.

*Apex*.—Acuminate.

*Base*.—Cuneate.

*Margin*.—Serrate.

*Thickness*.—Medium.

*Surface texture*.—Upper surface relatively smooth, slight indentations over midrib and leaf veins. Lower surface relatively smooth, except for small ridges created by midrib and pinnate venation. Both upper and lower surfaces glabrous.

*Petiole*.—Average length 12.5 mm. Average width 1.7 mm. Longitudinally grooved, surface glabrous. Color varies from 2.5GY 6/6 to 2.5GY 7/6.

*Glands*.—Type — reniform. Size — medium. Average length 1.3 mm. Average diameter 0.7 mm. Number varies from 1 to 6, average number 4. Located primarily on the base of the leaf blade and the upper portion of the petiole. Color varies from 2.5GY 5/4 to 2.5GY 5/6.

*Stipules*.—None present at time of measurement.

*Color*.—Upper surface varies from 5GY 4/4 to 5GY 3/2. Lower surface varies from 5GY 5/4 to 5GY 4/4. Midvein color varies from 2.5GY 8/2 to 5GY 7/2.

Flower buds:

*Size*.—Large. Average length 18.8 mm. Average diameter 9.2 mm.

*Hardiness*.—Hardy in all stone fruit growing areas of California.

*Density*.—Medium dense.

*Form*.—Conical, becoming elongated before opening.

*Pedicel*.—Average length 3.6 mm. Average width 1.2 mm. Color varies from 2.5GY 6/8 to 2.5GY 5/8. Surface glabrous.

*Color*.—Varies from 5RP 8/6 to 7.5RP 6/12.

Flowers:

*Blooming period*.—Date of First Bloom Mar. 2, 2014. Date of Petal Fall Mar. 12, 2014, varies slightly with climatic conditions.

*Size*.—Large, showy. Average height 22.3 mm. Average diameter 42.8 mm.

*Petals*.—Normally 5, alternately arranged to sepals. Size — large. Average length 23.6 mm. Average width 16.5 mm. Shape varies from elliptic to orbicular. Apex — rounded. Base — rounded to somewhat truncate. Margin — sinuate, slightly cupped. Both upper and lower surfaces glabrous. Color varies from 5RP 7/6 to 5RP 9/2, fades with age of flower.

*Petal arrangement*.—Free.

*Sepals*.—Normally 5, alternately arranged to petals. Average length 5.9 mm. Average width 5.1 mm. Shape — ovate, apex rounded. Margin — entire. Surface — upper surface glabrous, lower surface pubescent. Color — upper surface varies from 5GY 4/6 to 2.5R 3/6. Lower surface varies from 2.5R 2/4 to 5R 2/4.

*Stamens*.—Average number per flower 40. Average filament length 16.2 mm. On average, the stamens are below the height of the petals. Filament color varies from N 9.5/ (white) to 10R 3/10. Anther color varies from 7.5R 4/10 to 10R 3/10.

*Pollen*.—Self fertile. Color varies from 5Y 7/8 to 5Y 7/10.

*Pistil*.—Normally one. Surface — pubescent. Average length 19.4 mm. Position of stigma an average of 0.8 mm below the anthers. Color varies from 2.5GY 8/6 to 2.5GY 7/6.

*Fragrance*.—Very slight.

*Color*.—Varies from 5RP 8/4 to 5RP 7/6.

*Number flowers per flower bud*.—Normally one.

*Pedicel*.—Average length 4.4 mm. Average width 1.2 mm. Color varies from 2.5GY 8/6 to 2.5GY. Surface glabrous.

Fruit:

*Maturity when described*.—Firm ripe and ready for consumption.

*Date of first picking*.—Aug. 30, 2014.

*Date of last picking*.—Sep. 6, 2014, varies slightly with climatic conditions.

*Size*.—Large. Average diameter axially 70.3 mm. Average transversely in suture plane 78.9 mm. Average weight 269.8 grams, varies slightly with fertility of the soil, amount of thinning and climatic conditions.

*Form*.—Globose.

*Suture*.—Slightly lipped, extent varies slightly between fruit.

*Apex*.—Varies from rounded to slight tip.

*Base*.—Slightly retuse.

*Stem cavity*.—Rounded to slightly elongated in suture plane. Average depth 6.9 mm. Average diameter 12.5 mm.

Stem:

*Size*.—Small. Average length 9.9 mm. Average diameter 3.7 mm.

*Color*.—Varies from 7.5Y 7/8 to 10Y 7/6.

Flesh:

*Ripens*.—Evenly.

*Texture*.—Firm, meaty.

*Fibers*.—Few, small, tender.

*Firmness*.—Firm, holds firm on the tree 7 to 8 days past maturity (shipping ripe).

*Aroma*.—Slight.

*Amydgalin*.—Undetected.

*Eating quality*.—Very good.

*Flavor*.—Very good, mild, sweet, subacid flavor.

*Juice*.—Moderate amount, enhances flavor.

*Acidity*.—Not available.

*Brix*.—Average Brix 14.4°, varies slightly with amount of fruit per tree and climatic conditions.

*Pit cavity*.—Average length 34.8 mm. Average width 24.6 mm. Average depth 18.6 mm. Color varies from 5R 2/2 to 7.5R 2/8.

*Color*.—Varies from 10Y 9/2 to 10YR 9/1, with 10R 9/2 bleeding outward from the pit cavity.

Skin:

*Thickness*.—Medium.

*Surface*.—Smooth.

*Pubescence*.—Moderate amount, short in length.

*Tendency to crack*.—None.

*Color*.—Ground color varies from 5Y 9/2 to 7.5YR 9/2. Overspread with 5R 3/6 to 5R 7/6.

*Tenacity*.—Tenacious to flesh.

*Astringency*.—None.

Stone:

*Type*.—Clingstone, strong adherence.

*Size*.—Large. Average length 33.9 mm. Average width 24.0 mm. Average thickness 17.9 mm.

*Form*.—Ovoid.

*Base*.—Flat.

*Apex*.—Pointed. Average length 2.4 mm.

*Surface*.—Pitted throughout, pits vary from rounded to elongated. One furrow on each side of suture.

*Sides*.—Unequal with one side extending slightly further from suture plane.

*Ridges*.—Relatively smooth, extending from base toward apex.

*Tendency to split*.—None.

*Color*.—Varies from 5R 2/4 to 7.5R 2/4 when dry.

Kernel:

*Size*.—Average length 18.3 mm. Average width 11.4 mm. Average depth 6.4 mm.

*Form*.—Ovoid.

*Viability*.—Viable, complete embryo development.

*Skin color*.—Varies from 7.5YR 3/6 to 7.5YR 4/8.

Use: Dessert.

*Market*.—Local and long distance.

Keeping quality: Good, held firm in cold storage for 2 weeks at 38° to 42° F. without internal breakdown or appreciable loss of flavor.

Shipping quality: Good, showed minimal skin scarring or bruising of flesh during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program. No atypical resistances/susceptibilities have been noted under normal cultural practices.

The present new variety of peach tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of peach tree, (*Prunus persica*) substantially as illustrated and described.

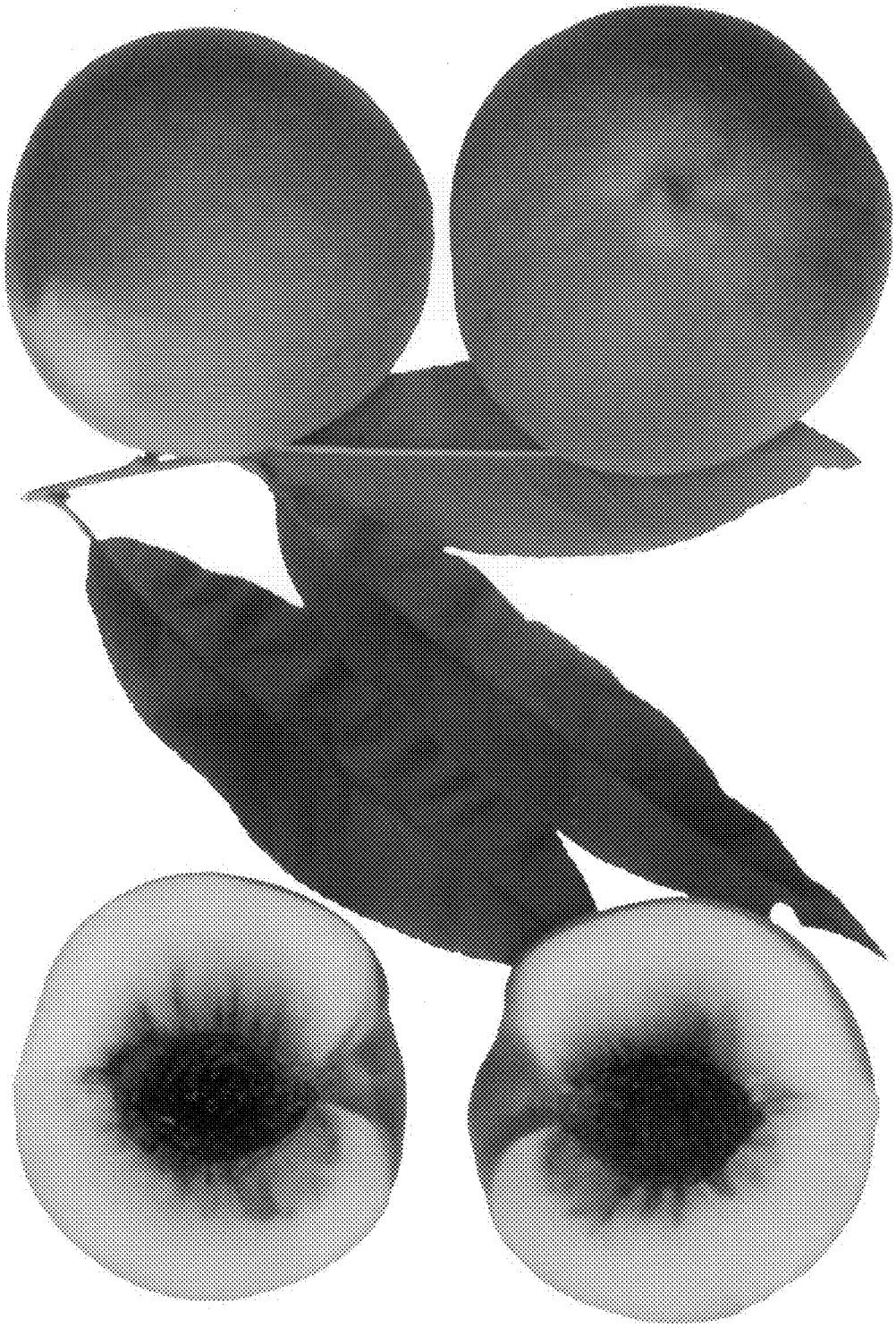

* * * * *